(12) United States Patent
Shan et al.

(10) Patent No.: US 12,076,711 B2
(45) Date of Patent: Sep. 3, 2024

(54) HYDROCARBON CONVERSION PROCESSES USING METAL CARBIDE NANOMATERIAL CATALYSTS

(71) Applicants: CHINA ENERGY INVESTMENT CORPORATION LIMITED, Beijing (CN); NATIONAL INSTITUTE OF CLEAN-AND-LOW-CARBON ENERGY, Beijing (CN)

(72) Inventors: Junjun Shan, Mountain View, CA (US); Hui Wang, Mountain View, CA (US); Lisa Nguyen, Mountain View, CA (US); Joshua Miles, Mountain View, CA (US); Jihong Cheng, Mountain View, CA (US)

(73) Assignees: China Energy Investment Corporation Limited, Beijing (CN); National Institute of Clean-And-Low-Carbon Energy, Beijing (CN)

( * ) Notice: Subject to any disclaimer, the term of this patent is extended or adjusted under 35 U.S.C. 154(b) by 443 days.

(21) Appl. No.: 16/744,371

(22) Filed: Jan. 16, 2020

(65) Prior Publication Data
US 2020/0246783 A1 Aug. 6, 2020

Related U.S. Application Data

(60) Provisional application No. 62/800,662, filed on Feb. 4, 2019.

(51) Int. Cl.
*B01J 27/22* (2006.01)
*B01J 6/00* (2006.01)
(Continued)

(52) U.S. Cl.
CPC .............. *B01J 27/22* (2013.01); *B01J 6/001* (2013.01); *B01J 29/40* (2013.01); *B01J 35/397* (2024.01);
(Continued)

(58) Field of Classification Search
None
See application file for complete search history.

(56) References Cited

U.S. PATENT DOCUMENTS

| 7,153,807 | B2 | 12/2006 | Molinier et al. |
| 8,946,107 | B2 | 2/2015 | Lauritzen et al. |

(Continued)

FOREIGN PATENT DOCUMENTS

| CN | 101371988 A | 2/2009 |
| CN | 101678341 | 3/2010 |

(Continued)

OTHER PUBLICATIONS

Element Summary, PubChem, https://pubchem.ncbi.nlm.nih.gov/element/Platinum#section=Element-Symbol (Year: 1964).*

(Continued)

*Primary Examiner* — Melissa S Swain
*Assistant Examiner* — Keling Zhang
(74) *Attorney, Agent, or Firm* — Calfee, Halter & Griswold LLP

(57) ABSTRACT

A catalyst that includes heterogeneous metal carbide nanomaterials and a novel preparation method to synthesize the metal carbide nanomaterials under relatively mild conditions to form an encapsulated transition metal and/or transition metal carbide nanoclusters in a support and/or binder. The catalyst may include confined platinum carbide nanoclusters. The preparation may include the treatment of encapsulated platinum nanoclusters with ethane at elevated temperatures. The catalysts may be used for catalytic hydro- (Continued)

carbon conversions, which include but are not limited to, ethane aromatization, and for selective hydrogenation, with negligible green oil production.

4 Claims, 6 Drawing Sheets

(51) Int. Cl.
```
B01J 29/40      (2006.01)
B01J 35/30      (2024.01)
B01J 35/40      (2024.01)
B01J 35/60      (2024.01)
B01J 37/00      (2006.01)
B01J 37/04      (2006.01)
B01J 37/16      (2006.01)
C07C 5/09       (2006.01)
C07C 11/04      (2006.01)
```

(52) U.S. Cl.
CPC ............ *B01J 35/398* (2024.01); *B01J 35/40* (2024.01); *B01J 35/60* (2024.01); *B01J 37/0009* (2013.01); *B01J 37/04* (2013.01); *B01J 37/16* (2013.01); *C07C 5/09* (2013.01); *C07C 11/04* (2013.01)

(56) References Cited

U.S. PATENT DOCUMENTS

| | | |
|---|---|---|
| 9,533,288 B2 | 1/2017 | Dufresne et al. |
| 2004/0176652 A1 | 9/2004 | Molinier et al. |
| 2010/0137125 A1 | 6/2010 | Ma et al. |
| 2013/0066126 A1 | 3/2013 | Jana |
| 2015/0018438 A1 | 1/2015 | Ha et al. |
| 2016/0096167 A1 | 4/2016 | Park et al. |
| 2016/0121314 A1 | 5/2016 | Jana |
| 2018/0194701 A1 | 7/2018 | Hong |

FOREIGN PATENT DOCUMENTS

| | | | |
|---|---|---|---|
| CN | 102604668 A | 7/2012 | |
| CN | 102971075 A | 3/2013 | |
| CN | 103566965 A | 2/2014 | |
| CN | 103657633 A | 3/2014 | |
| CN | 104226354 A | 12/2014 | |
| CN | 104857983 A | 8/2015 | |
| CN | 105582913 B | 1/2018 | |
| CN | 107983272 A | 5/2018 | |
| KR | 20110004726 A | 1/2011 | |
| WO | WO-9400232 A1 * | 1/1994 | ............ B01J 23/96 |

OTHER PUBLICATIONS

Bernhard et al., Influence of platinum dispersion on the hydrodearomatization of toluene to light alkanes on Pt/H-ZSM-5, Catalysis Communication, 2011, 12, 757-760 (Year: 2011).*

L. Melo et al., Acetone Transformation Over Pt/H[A1]ZSM5 and Pt/H[Ga]ZSM5 Catalysts Evidences of a Pt—Ga Interaction, Journal of Molecular Catalysis A: Chemical 177, (2002), pp. 281-287.

International Search Report and Written Opinion in corresponding PCT Application No. PCT/CN2020/074290, dated Apr. 29, 2020.

Adolfo Arcoya et al., Surface Characterization and Dehydrocyclization Activity of Pt/KL Catalysts Prepared by Different Methods, Applied Surface Science 205 (2003), pp. 206-211.

International Search Report and Written Opinion in corresponding PCT Application No. PCT/CN2020/074291, dated May 6, 2020.

Shuai Tan et al., Active Site and Electronic Structure Elucidation of Pt Nanoparticles Supported on Phase-Pure Molybdenum Carbide Nanotubes, ACS Applied Material & Interfaces, Mar. 6, 2017, 9, pp. 9815-9822.

Patanachai Janthon et al., Carbon Dissolution and Segregation in Platinum, Catalysis Science & Technology, Jan. 20, 2017, 7, pp. 807-816.

Yizhi Xiang et al., Progress and Prospects in Catalytic Ethane Aromatization, Catalysis Science & Technology, Royal Society of Chemistry, Feb. 14, 2018, pp. 1-17.

Shigeaki Ono et al., A High-Pressure and High-Temperature Synthesis of Platinum Carbide, Solid State Communications, 133, Oct. 5, 2004, pp. 55-59.

Detre Teschner et al., The Roles of Subsurface Carbon and Hydrogen in Palladium-Catalyzed Alkyne Hydrogenation, Science, vol. 320, Apr. 4, 2008, pp. 86-90.

Huabin Zhang, Dynamic Traction of Lattice-Confined Platinum Atoms into Mesoporous Carbon Matrix for Hydrogen Evolution Reaction, Science Advances, Jan. 19, 2018, 4:eaao6657, pp. 1-9.

Lichen Liu et al., Generation of Subnanometric Platinum with High Stability during Transformation of a 2D Zeolite into 3D, Nature Materials, vol. 16, Sep. 26, 2016, pp. 132-142.

Vasudeo P. Babar et al., Interaction of a Carbon Atom on Small Platinum Clusters and its Effects on Hydrogen Binding, Chemical Physics Letters, 560 (2013), pp. 42-48.

Wang et al., "In situ encapsulation of platinum clusters within H-ZSM-5 zeolite for highly stable benzene methylation catalysis," Catalysis Science & Technology, 2017, pp. 6140-6150.

Office Action from Chinese Application No. 202010079965.X dated Mar. 2, 2022.

English translation of Office Action from Chinese Application No. 202010079963.0 dated May 25, 2022.

* cited by examiner

HYDROCARBON CONVERSION PROCESSES USING METAL CARBIDE NANOMATERIAL CATALYSTS

CROSS REFERENCE TO RELATED APPLICATIONS

This application claims the benefit of U.S. provisional application No. 62/800,662, filed Feb. 4, 2019, titled "METAL CARBIDE NANOMATERIALS, METHOD OF PREPARATION, AND CATALYTIC APPLICATIONS THEREOF," which is incorporated herein by reference.

FIELD OF THE INVENTION

The present invention relates to hydrocarbon conversion catalysts and production methods thereof, and more particularly relates to the synthesis of a novel nanomaterial catalyst that includes encapsulated metal carbide nanoclusters, where the metal carbide nanoclusters are prepared through the treatment of confined metal nanoclusters with hydrocarbons at relatively mild conditions, e.g., temperatures between 100-700° C. and atmospheric conditions.

The present invention also relates to catalytic processes for hydrocarbon conversions that use the novel metal carbide nanomaterial, where the catalytic material comprises confined metal carbide nanoclusters which are highly active for hydrocarbon conversions, where the metal in the metal carbide is a transition metal.

BACKGROUND OF THE INVENTION

Metal carbide based catalytic materials have attracted considerable attention in recent years, due to their unique catalytic properties in many reactions. For example, Science 320 (2008) 86-89 reported that a catalytic material of palladium (Pd) carbide catalyst can catalyze the alkyne hydrogenation selectivity. The presence of carbon in the catalyst plays a key role in governing the product selectivity. Catalysis Science & Technology 7 (2017) 807-816 demonstrated that it is feasible to synthesize platinum (Pt) carbide nanomaterials where such materials exhibit unique catalytic properties. However, in reality, Pt carbide materials have only been successfully synthesized under rather extreme, e.g., high temperature and high pressure, conditions. For instance, Solid State Communications 133 (2005) 55-59 teaches that Pt carbide materials can be synthesized through high-pressure, high-temperature treatment of Pt powder supported on a laser-heated diamond anvil cell. High-pressure X-ray diffraction experiments confirmed that at synthesizing conditions of 85 GPa and 2600 K, the Pt carbide structure can be formed through the interaction of Pt with the carbon support.

However, the Pt carbide materials prepared through high pressure and high temperature treatment is not only costly, but has had very limited applications. It is desirable to develop a new synthesis method that can be used to prepare Pt carbide materials under relatively mild conditions.

The shale-gas boom in the United States has also provided an opportunity to develop advanced catalysts and processes for hydrocarbon conversions, for example, as taught in U.S. Pat. Nos. 7,153,807 and 8,946,107 and U.S. publication 2018/0194701, which are incorporated by reference herein. In practice, most catalytic processes are based on heterogeneous catalysts. Comparing to homogeneous catalytic materials, heterogeneous catalytic materials are easier to prepare, ship, and handle, as well as often being more stable and cheaper to manufacture.

For example, light olefins, e.g., ethylene, propylene, and butene, are widely used in polymerization industries. These olefin products often contain unsaturated alkyne and alkadiene impurities, such as acetylene and butadiene, which are by-products generated through steam cracking or fluid catalytic cracking. The presence of such impurities typically poison polymerization catalytic materials, thus must be removed. Generally, selective hydrogenation of alkynes and alkadienes to olefin is the most attractive solution for industrial plants. Accordingly, palladium-based catalysts have been extensively studied and widely used for such hydrogenation reactions.

However, current commercial Pd-based catalysts suffer from the problems of producing significant amounts of saturates and green oil (C4+ oligomer compounds), as by-products, which are produced from over-hydrogenation of olefins and/or oligomerization of the alkynes and/or alkadienes and/or olefins. This green oil by-product is undesirable owing to its adverse effect on olefins-gain selectivity. More importantly, the green oil also deposits C4+ compounds on the hydrogenation catalyst surface which poisons the catalysts. In other words, the green oil decreases the lifetime of the hydrogenation catalysts, e.g., making the catalyst unable to effectively aid in the hydrocarbon reactions. Thus, it is highly desirable to develop new catalysts that can selectively hydrogenate alkynes and alkadienes to olefin with reduced green oil productivity.

U.S. Pat. No. 7,153,807 discloses Pt based PtIr and PtRu bimetallic catalysts, as well as PtRuAg trimetallic catalysts for the selective hydrogenation of alkynes and alkadienes to olefin with low green oil selectivity. U.S. Pat. No. 7,153,807 also describes the process for the selective hydrogenation of alkynes and alkadienes to olefin using the PtIr and PtRu bimetallic catalysts, as well as PtRuAg trimetallic catalysts, supported on silica or alumina supports. These Pt based catalysts show high activity towards acetylene hydrogenation, but with reduced green oil selectivity comparing to commercial Pd-based catalysts. Furthermore, additional benefits of these Pt based catalysts also include the extended lifetime of the catalysts or the extension of the operation cycle owing to the suppression of green oil productivity, which reduces the poisoning of the catalyst U.S. publication 2004/0176652 also teaches Pt based PtRu, PtRuAg, and PtRuGa catalysts supported on alumina which are used in a dual bed process to selectively hydrogenate alkynes and alkadienes to olefin. U.S. Pat. No. 9,533,288 describes the preparation of a Pt based metal catalyst where a layer of Ni is electroplated on a metallic support which then has an electroplated top layer of Pt. This Pt based supported metal catalyst exhibits high activity towards the selective hydrogenation of unsaturated hydrocarbons.

Table 1 shows the testing results reported in U.S. Pat. No. 7,153,807 of such Pt-based catalysts. Comparing to commercial Pd/Ag based catalyst, 0.6% Pt on $Al_2O_3$ shows higher ethylene selectivity and slightly lower green oil selectivity, but much lower acetylene conversion. Although Ir itself is not active, by adding Ir to Pt, the acetylene conversion can be significantly enhanced, and green oil selectivity can be further decreased. However, in this case ethylene selectivity is largely reduced, which is a significant drawback of PtIr bimetallic catalyst. The similar performances were also observed for PtRu and PtRuAg catalysts. Overall, $Pt/Al_2O_3$ catalyst exhibits high ethylene selectivity but low acetylene conversion and high green oil productivity, whereas, Pt based bimetallic and trimetallic catalysts exhibit improved acetylene conversion and reduced green oil productivity, but much lower ethylene selectivity.

A good hydrogenation catalyst, however, must be able to minimize the green oil productivity while maintaining high activity and high ethylene selectivity. In so doing, the Pt based bimetallic and trimetallic catalysts described in U.S. Pat. No. 7,153,807 do not meet this criterion, nor do the catalysts disclosed in U.S. publication 2004/0176652 and U.S. Pat. No. 9,533,288.

TABLE 1

| Test # | Catalyst | $C_2H_2$ conversion (%) | $C_2H_4$ selectivity (%) | Green oil selectivity (%) |
|---|---|---|---|---|
| 1 | Commercial Pd/Ag based catalyst | 96.9 | 45 | 26.2 |
| 2 | 0.6% Pt on $Al_2O_3$ | 18.5 | 93.6 | 19.0 |
| 3 | 2.4% Ir on $Al_2O_3$ | 0.1 | N/A | N/A |
| 4 | 0.6% Pt, 2.4% Ir on $Al_2O_3$ | 31.9 | 30.5 | 16.0 |
| 5 | 1.2% Pt, 7.2% Ir on $Al_2O_3$ | 41.3 | 44.9 | 13.0 |
| 6 | 2.4% Pt, 7.2% Ir on $Al_2O_3$ | 43.3 | 7.1 | 7.5 |
| 7 | 0.6% Pt, 2.4% Ru on $Al_2O_3$ | 55.8 | 28.4 | 10.5 |
| 8 | 0.6% Pt, 2.4% Ir, 1.2% Ag on $Al_2O_3$ | 56.3 | 44.2 | 9.9 |

Furthermore, the direct conversion of ethane into aromatics is of great interest as an alternative way to produce light aromatics (benzene, toluene, xylenes, or BTX) from a cheap and abundant source. To date, noble metal modified zeolite catalysts have been widely studied in ethane aromatization, where these catalysts usually contain 0.02 to 0.5 wt % of metal loading with the noble metals.

Catalysis Science & Technology, 8 (2018) 1500-1516 provide a comprehensive exploration of early patents from industrial players as well as scientific papers in this field, particularly, the catalyst preparation and their catalytic performances in the direct conversion of ethane into aromatics. Additionally, U.S. Pat. No. 8,946,107 and U.S. publication 2018/0194701 disclose processes to selectively convert ethane to aromatic hydrocarbons based on Pt modified ZSM-5 catalysts.

For example, U.S. Pat. No. 8,946,107 discloses a method that uses Pt/ZSM-5 with Pt loading at 0.005 to 0.1 wt % to catalyze the ethane aromatization reaction. U.S. Pat. No. 8,946,107 also describes that adding a second metal such as Fe to the Pt, can reduce the undesired methane productivity. But such bimetallic catalysts also decrease the catalyst activity in terms of ethane conversion.

Although it has been reported that Pt/ZSM-5 based catalysts are active for ethane aromatization, the active phase and the chemical state of Pt during ethane aromatization has not been addressed in Catalysis Science & Technology, 8 (2018) 1500-1516, U.S. Pat. No. 8,946,107 and U.S. publication 2018/0194701, as well as in other literature. In other words, all previous studies of such catalysts have failed to provide the complete information regarding the catalyst formulation and active phase of Pt/ZSM-5 based catalysts in the ethane aromatization reaction. Accordingly, it would be advantageous to know the catalyst formulation and the optimal conditions for the active phase of such catalysts.

SUMMARY OF THE INVENTION

The present invention is provided to solve the deficiencies of the prior art by providing improvements over the prior art methods and catalysts in several ways. For example, the present invention provides catalysts that can selectively hydrogenate alkynes and alkadienes in the presence of other unsaturated compounds, methods for producing the catalysts, and methods for using the catalysts in catalytic applications.

In order to achieve the objectives of the present invention, a first aspect of the invention relates to catalysts that include new types of heterogeneous metal carbide nanomaterials that can be characterized with various techniques. The invention also relates to a novel preparation method to synthesize the metal carbide nanomaterials under relatively mild conditions to form an encapsulated noble metal and/or noble metal carbide nanoclusters in a support and/or binder, where the formation of these metal carbide nanomaterial under mild conditions has never been reported before in any available literature. For example, the catalysts include confined Pt carbide nanoclusters that is prepared through the treatment of encapsulated Pt nanoclusters with ethane at elevated temperatures.

A second aspect of the invention relates to using this novel type of heterogeneous metal carbide nanomaterial catalytic material, that includes confined or encapsulated metal carbide nanoclusters on a support and/or binder, for catalytic applications, which are highly active for selective hydrocarbon conversions, where the metal is preferably a noble metal.

In carrying out these and other objects of the invention, the metal carbide nanomaterial catalyst can contain one or more transition metals. Examples of a transition metal include, but are not limited to, platinum, copper, nickel, rhenium, tantalum, manganese, iridium, and osmium; preferably platinum. The transition metals are supported on at least one support and/or binder selected from, but not limited to, inorganic oxides, silicon carbide, silicon nitride, boron nitride, carbon, and combinations thereof, where preferably, the support is an aluminosilicate zeolite. Examples of the zeolite support include, but are not limited to, Zeolite Socony Mobil-5 (ZSM-5), ZSM-11, ZSM-12, ZSM-23, ZSM-35, mordenite (MOR), Ferrierite, Faujacite, Chabacite, beta zeolite (BEA), Y zeolite, X zeolite, SSZ-13, titanium silicalite-1 (TS-1), Amicite, Barrerite, Clinoptilolite, Harmotome, Laumontite, Paulingite, Pollucite, and mesoporous silica (e.g., MCM41).

The metal carbide nanomaterial catalyst can be used to catalyze the selective hydrocarbon conversions. For example, it was found that catalysts that contain the confined/encapsulated metal carbide nanoclusters can efficiently and selectively catalyze the hydrogenation of alkynes and alkadienes to olefins at near room temperatures, with high olefin selectivity and negligible green oil productivity. Additionally, it was found that the catalysts that include the confined metal carbide nanoclusters exhibit high activity towards the direct conversion of ethane into aromatics.

There are several benefits associated with using the present invention, which include the following:

1. Producing only negligible amounts of green oil, thus significantly increasing the lifetime of the catalyst.
2. Exhibiting much higher catalytic activity than the standard Pt/$Al_2O_3$ catalyst at the same reaction conditions, while maintaining the same ethylene selectivity.

BRIEF DESCRIPTION OF THE DRAWINGS

The accompanying drawings herein are used to provide further understanding of the invention and constitute a part of the description. The accompanying drawings together with the following embodiments serve to explain the invention, but do not constitute a limitation to the invention. In the accompanying drawings.

Figure 1:
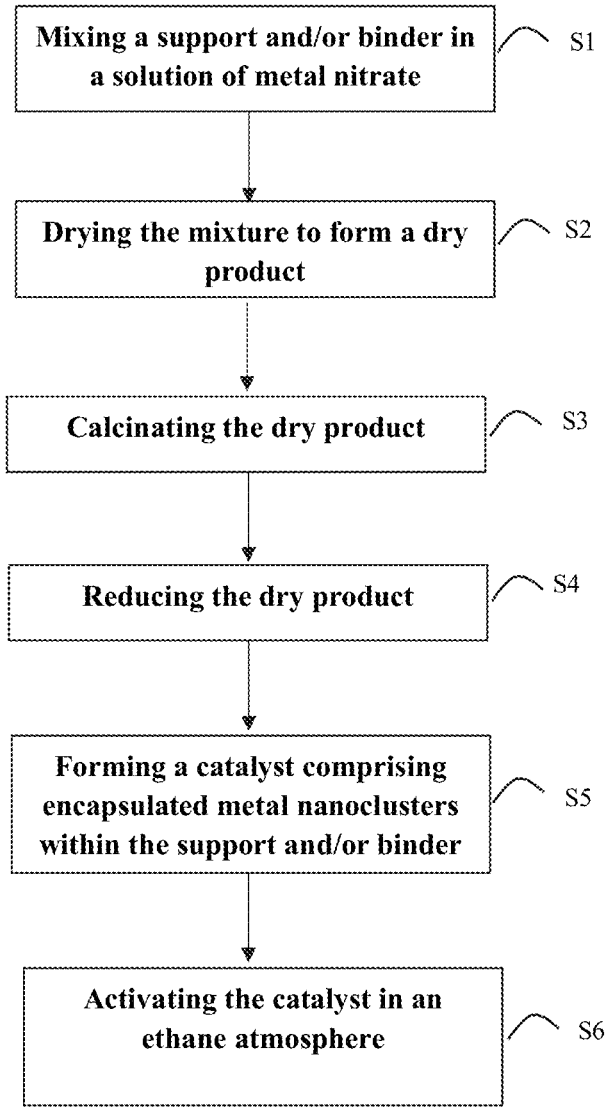
FIG. 1 is a schematic representation of the process for forming the metal nanomaterial catalyst.

In the various figures, similar elements are provided with similar reference numbers. It should be noted that the drawing figures are not necessarily drawn to scale, or proportion, but instead are drawn to provide a better understanding of the components thereof, and are not intended to be limiting in scope, but rather provide exemplary illustrations, and graphs are drawn to present the relevant data.

DETAILED DESCRIPTION OF THE INVENTION

The embodiments of the invention will be described below in detail with reference to the accompanying drawings. It should be understood that embodiments described herein are only for illustration and explanation of the invention, but not for limitation to the invention.

The present invention relates to a method for synthesizing supported catalysts, where the active phase is at the surface or within pores of the solid support, where the novel supported catalysts are capable of delivering selective hydrogenation performance with high olefin-gain selectivity and low selectivity to green oil (oligomers) and/or saturates, and to catalysts obtained from this method. In so doing, the present invention at least has the benefits of the increase in life expectancy of the catalysts and/or increased catalytic activity.

As seen in FIG. 1, in one embodiment of the invention, a method is provided for synthesizing the novel heterogenous catalyst that comprises at least some of the following steps:

Step 1 (S1): mixing a support and/or binder in a solution of metal precursor, preferably metal nitrate, to form a mixture;

Step 2 (S2): drying the mixture to form a dry product;

Step 3 (S3): calcinating the dry product;

Step 4 (S4): reducing the dry product;

Step 5 (S5): forming a catalyst comprising encapsulated metal nanoclusters within the support and/or binder; and Step 6 (S6): preferably, but not necessarily, activating the catalyst in an ethane atmosphere.

Specifically, in the mixing step S1, the support and/or binder is selected from inorganic oxides, silicon carbide, silicon nitride, boron nitride, carbon, zeolites and combinations thereof, where preferably, the support is an aluminosilicate zeolite, which includes but is not limited to, ZSM-5, ZSM-11, ZSM-12, ZSM-23, ZSM-35, MOR, Ferrierite, Faujacite, Chabacite, beta zeolite (BEA), Y zeolite, X zeolite, SSZ-13, titanium silicalite-1 (TS-1), Amicite, Barrerite, Clinoptilolite, Harmotome, Laumontite, Paulingite, Pollucite, and mesoporous silica (e.g., MCM41), preferably ZSM-5, having a silica to alumina ratio of between 10:1 to 80:1, preferably between 20:1 to 45:1, and most preferably 30:1. The support and/or binder is mixed with an aqueous solution, which contains metal precursor, preferably platinum nitrate, which includes salts and complexes of platinum, where the mixture is mixed at moderate temperatures, e.g., 10-100° C., preferably 80° C., and ambient pressures, e.g., standard atmospheric pressure 101.3 kPA.

The mixture is then dried at step S2 to obtain a dry product, where the dry product is then air calcinated at elevated temperatures at step S3, for example, between 300-800° C., and preferably at 550° C., for a certain period, preferably 0.5 to 24 hours, more preferably four hours. It is appreciated that during the air calcination step S3, inert binders such as silica powder and/or alumina powder can be added before or after the air calcination step to improve the catalyst strength. After air calcination, the product is in-situ reduced in hydrogen in step S4 at elevated temperatures, for example, 300-800° C., and preferably at 630° C., for a certain period, preferably 0.5 to 24 hours, more preferably one hour, and then cooled to room temperature, e.g., between 20-25° C. in a hydrogen atmosphere, to provide the synthesized catalyst in step S5.

Optionally, after the in-situ reduction, at step S6, the product is cooled down to 100-650° C., preferably to 300-500° C., more preferably to 400° C., in the hydrogen atmosphere, which is followed by purging with an inert gas, e.g., nitrogen, at a temperature between 300-500° C., preferably 400° C., and activation in an atmosphere comprising at least one carbon-containing molecule, e.g., $CO_x$, $CS_x$, $C_xH_y$, $C_xH_yCl_z$, $C_xH_yF_z$, $C_xH_yBr_z$, $C_xH_yI_z$, $C_xH_yO_z$, and preferably ethane, and nitrogen (e.g., 50% balanced in nitrogen) at a temperature between 100-750° C., and preferably between 300-750° C., more preferably at 400° C., for a certain period of time. After the activation, the catalyst is cooled down to between 80-150° C., preferably to 100° C., using the carbon-containing molecule atmosphere, and then further cooled down to room temperature in an inert atmosphere, e.g., in nitrogen.

The resulting hydrogenation catalyst is a heterogeneous catalyst that includes the metal nanoclusters on the support and/or binder, and more preferably platinum or platinum carbide nanoclusters on an aluminosilicate zeolite, where the metal or metal carbide nanoclusters are confined or encapsulated in micropores of the zeolite. For example, the metal or metal carbide nanoclusters have sizes close to 1 nm, e.g., +/−10%, to be encapsulated in the zeolite. In one embodiment of the invention, the catalyst contains between 300-25000 ppm of platinum, and most preferably 500 ppm of platinum, where the platinum has a metal dispersion greater than 90% and preferably between 95-100%.

The inventive method and catalyst will be further illustrated with respect to specific Examples that are only intended to demonstrate the invention, but not limit it in any way.

Comparative Example 1

5 grams of $Al_2O_3$ powder was mixed with an amount of a $Pt(NO_3)_2$ containing solution. The mixture was stirred at room temperature for 1 hour and then heated to 80° C. for 1 hour in a rotary evaporator to obtain a dry product, followed by air calcination at 550° C. for 4 hours. The powder was then in-situ reduced in hydrogen at 630° C. for 1 hour, and cooled down to room temperature in a hydrogen atmosphere. The powder was then pressed and sized to 20×40 mesh. The obtained product is denoted as Catalyst A, which contains 500 ppm Pt. Catalyst A was then subjected to characterization measurements to determine its features.

Example 1

5 g of ZSM-5 powder (having a silica to alumina ratio of 30) was mixed with a certain amount of $Pt(NO_3)_2$ in solution. The mixture was agitated at room temperature for 1 hour and then heated to 80° C. in a rotary evaporator to obtain a dry product, which was followed by air calcination at 550° C. for 4 hours. The powder was then in-situ reduced in hydrogen at 630° C. for 1 hour, and cooled down to room temperature (e.g., between 20-25° C.) in a hydrogen atmosphere. The powder was then pressed and sized to 20×40 mesh. The obtained product is denoted as catalyst B, which contains 500 ppm Pt. Catalyst B was then subjected to characterization measurements to determine its features.

Example 2

A powder was prepared using the same procedure for Catalyst B from Example 1, but after the reduction in the hydrogen atmosphere, the powder was cooled to 400° C. in a hydrogen atmosphere, followed by a an inert gas purge at 400° C. for 10 minutes and then activated in ethane (50% balance in nitrogen) at a temperature between 300-500° C. After the ethane activation, the powder was cooled down to 100° C. under ethane flow, and further cooled to room temperature in an inert gas atmosphere, e.g., in nitrogen. The obtained product is denoted as catalyst C, which also contains 500 ppm platinum.

Catalysts A, B, and C were then characterized by testing and analyzing the catalysts for the platinum dispersion in the catalyst by dynamic CO chemisorption measurements (chemical adsorption), where the evolution of the platinum species was also studied by diffuse reflectance infrared Fourier transform spectroscopy (DRIFTS), and X-ray absorption near edge structure (XANES). As will be discussed below, the characterization data show for catalyst B, after reduction, the platinum forms encapsulated Pt small nanoclusters. Additionally, after ethane activation (catalyst C), these Pt nanoclusters are transformed to novel encapsulated Pt carbide nanoclusters, $PtC_x$/ZSM-5. The data also shows that adding inert binder does not affect such transformation, in other words does not affect the formation of Pt nanoclusters to Pt carbide nanoclusters.

Figure 2:
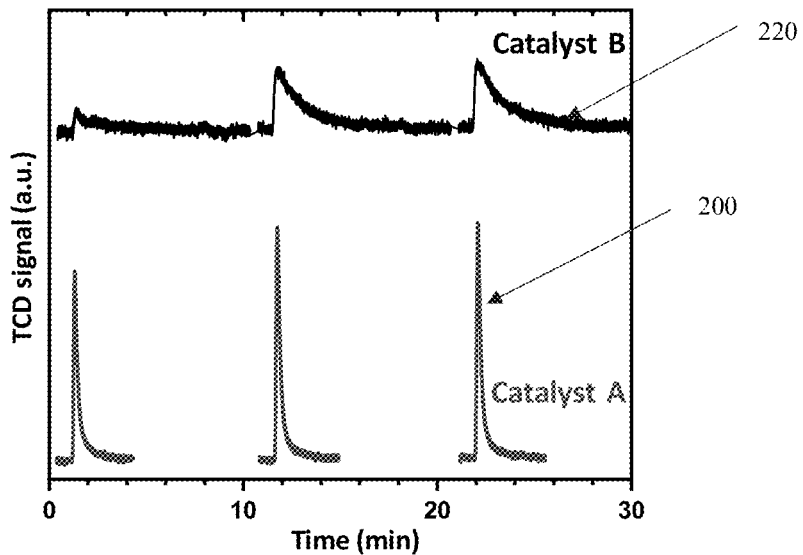
FIG. 2 is a graph of a comparison of the dynamic CO chemisorption data of a prior art catalyst ($Pt/Al_2O_3$ after reduction) and a catalyst embodied by a first aspect of the invention after in-situ hydrogen reduction at 630° C. (Pt/ZSM-5 after reduction).

FIG. 2 shows the dynamic CO chemisorption data of catalyst A (curve 200) after in-situ hydrogen reduction at 630° C. and catalyst B (curve 220) after in-situ hydrogen reduction at 630° C. The Pt dispersion and average particle size determined from the dynamic CO chemisorption are listed in Table 2. FIG. 2 and Table 2 show that for catalyst A, $Pt/Al_2O_3$, after hydrogen reduction, Pt dispersion is approximately 21%, and Pt mainly forms nanoparticles with the average particle size at 6 nm. On the other hand, for catalyst B after reduction, the data shows that the Pt dispersion is at ~100%, and the platinum forms small nanoclusters with the cluster size close to 1 nm. Moreover, the data shows that catalyst B has much larger peak widths which indicates that these nanoclusters are located within micropores of the zeolite. In other words, the data shows that after reduction, catalyst B includes encapsulated platinum nanoclusters in the zeolite support.

Figure 3:
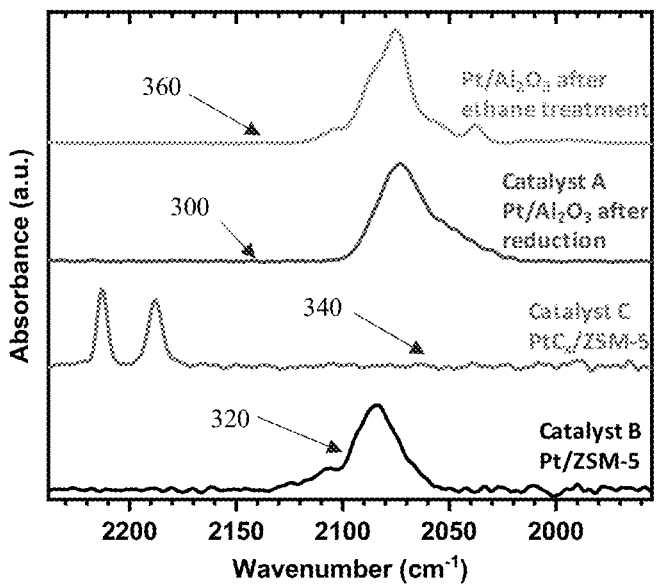
FIG. 3 is graph of a comparison of the CO-DRIFT spectra of a prior art catalyst ($Pt/Al_2O_3$ after reduction), a catalyst embodied by the first aspect of the invention (Pt/ZSM-5 after reduction), a catalyst embodied by a second aspect of the invention (Pt/ZSM-5 after ethane activation); and a prior art catalyst after ethane activation ($Pt/Al_2O_3$ after ethane treatment).

FIG. 3 shows the CO-DRIFT spectra of catalyst A after reduction ($Pt/Al_2O_3$ after reduction) (curve 300), catalyst B after reduction (Pt/ZSM-5 after reduction) (curve 320), and catalyst C (Pt/ZSM-5 after ethane activation) (curve 340), as well as an example of catalyst A after the ethane treatment ("modified catalyst A") (curve 360). In the case of catalyst A and catalyst B, the sample was first reduced with hydrogen at 630° C., and then cooled down to room temperature in a helium atmosphere, followed by the CO-DRIFTS measurements at room temperature. In the case of catalyst C and modified catalyst A, after the same treatment, the catalysts were cooled down to 100° C. in ethane, followed by further cooling down to room temperature in helium. CO-DRIFTS measurements at room temperature were performed after an additional helium purge for 30 min.

The CO-DRIFTS measurements in FIG. 3 shows that for catalyst A after reduction, Pt forms metallic nanoparticles, which is consistent with the dynamic CO chemisorption measurements in FIG. 2. However, for catalyst B after reduction, CO-DRIFTS and dynamic CO chemisorption data show that the majority of the platinum forms Pt small nanoclusters encapsulated within micropores of zeolite. Furthermore, CO-DRIFT spectra also show that after ethane activation, the peak related to Pt nanoclusters completely disappears, while a new double peak feature in the range from 2250 $cm^{-1}$ to 2150 $cm^{-1}$ appears. Similar double peak feature has been reported in CO-DRIFTS study of molybdenum carbide materials (ACS Applied Materials & Interfaces, 9 (2017) 9815-9822). Thus, it is understood that in combination with other characterizations listed below, this double peak feature may be related to the presence of platinum carbide nanoclusters. Therefore, it can be concluded that the encapsulated Pt nanoclusters presented in Pt/ZSM-5 after reduction were transformed to encapsulated Pt carbide nanoclusters in catalyst C, Pt/ZSM-5 after ethane activation. On the other hand, FIG. 3 also shows that for catalyst A after similar ethane treatment, there is no presence of such double peak feature as catalyst C indicating that large Pt metallic nanoparticles cannot be transformed to Pt carbide species upon ethane treatment.

Figure 4:
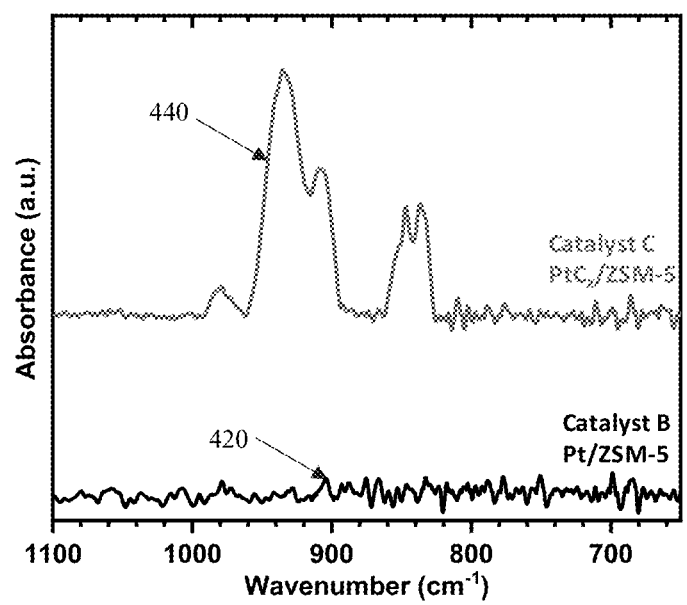
FIG. 4 is a graph illustrating the FTIR spectra of a catalyst embodied by the first aspect of the invention (Pt/ZSM-5 after reduction) and a catalyst embodied by the second aspect of the invention (Pt/ZSM-5 after ethane activation).

FIG. 4 shows the FTIR spectra of catalyst B after reduction, (Pt/ZSM-5 after reduction) (curve 420) and catalyst C (Pt/ZSM-5 after ethane activation) (curve 440). In the case of catalyst B, after reduction, the sample was cooled down to room temperature in helium, followed by the FTIR measurements at room temperature. In the case of catalyst C, after ethane activation, the sample was first cooled down to 100° C. in ethane, and then was further cooled down to room temperature in helium, followed by helium purge at room temperature for 30 min, prior to FTIR measurements.

As seen in FIG. 4, the FTIR spectra in the Pt—C stretching range for catalyst B shows clearly, after reduction, there is no peak associated with Pt—C bonds. However, after ethane activation, there are several peaks associated with the Pt—C bonds for catalyst C, as reported in the literature (Chemical Physics Letters, 560 (2013) 42-48). Thus the in-situ FTIR data shows that upon ethane activation, there are Pt carbide species in catalyst C.

Figure 5:
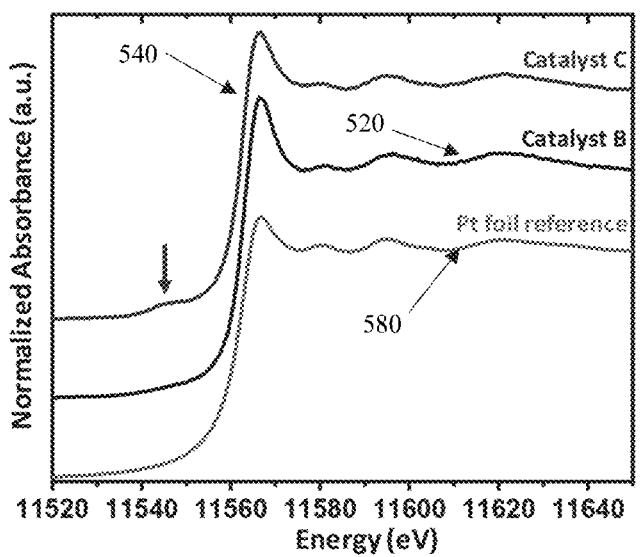
FIG. 5 is a graph illustrating the in-situ XANES spectra of a catalyst embodied by the first aspect of the invention (Pt/ZSM-5 after reduction) and a catalyst embodied by the second aspect of the invention (Pt/ZSM-5 after ethane activation), as well as Pt foil as a reference.

FIG. 5 shows the in-situ XANES spectra of catalysts B after reduction, (Pt/ZSM-5 after reduction) (curve 520) and catalyst C (Pt/ZSM-5 after ethane activation) (curve 540), as well as a Pt foil as a reference (curve 580). In the case of catalyst B, after reduction, the sample was cooled down to room temperature in helium, followed by XANES measurements at room temperature. In the case of catalyst C, after ethane activation, the sample was first cooled down to 100° C. in ethane, and then was further cooled down to room temperature in He, followed by He purge at room temperature for 30 min, prior to XANES measurements.

The XANES data in FIG. 5 further supports that encapsulated Pt carbide nanoclusters are formed after ethane activation. For example, after reduction, the XANES spectrum of catalyst B is different than the Pt metallic foil, where a high intensity white line is present in the case of Pt/ZSM-5 after reduction. Similarly, such XANES spectra with a high intensity white line has been observed in a published study of canonic Pt small nanoclusters encapsulated within micropores of MCM-22 (Nature Materials, 16 (2017) 132-138). Thus, the XANES spectra also suggests that after reduction, Pt forms small nanoclusters in catalyst B. Moreover, after ethane activation, a new pre-edge peak between 11530-11560 eV appears in the XANES spectrum of catalyst C. A similar pre-edge peak of Pt has been reported in a published study of atomically dispersed Pt embedded in carbon matrix, and was attributed to the electronic effect on Pt caused by the presence of Pt—C bonds of confined Pt species (Science Advance, 4 (2018) eaao6657). It is very likely that the appearance of the pre-edge peak in catalyst C is also due to the electronic effect on Pt caused by the formation of Pt—C bonds. Thus, the XANES data also supports the conclusion on the transformation of Pt nanoclusters to Pt carbide nanoclusters upon ethane activation.

That is, the characterizations of these catalytic materials are shown in FIG. 2 to FIG. 5 and Table 2 (below).

TABLE 2

| Sample | Pt dispersion | Particle Size |
|---|---|---|
| Catalyst B, 0.05 wt % Pt/ZSM-5 | 100% | ~1 nm |
| Catalyst A, 0.05 wt % Pt/Al$_2$O$_3$ | 21% | 6 nm |

Such novel catalysts were found to be capable of delivering improved selective hydrogenation performance with high olefin-gain selectively and low selectivity to green oil and/or saturates during a hydrogen conversion process as known in the art. For example, hydrogen conversion processes as disclosed in U.S. Pat. Nos. 7,153,807 and 8,946,107 and U.S. publication 2018/0194701, which are incorporated herein by reference. In so doing, the benefits of the novel catalysts B and C include, but are not limited to, the extension of the lifetime performance of the catalyst and/or the extension of the operation cycle of the hydrogenation due to the reduction of green oil production.

In one embodiment of the invention, the ethane aromatization is performed at temperatures between between 300-750° C., preferably between 500-650° C., more preferably between 600-630° C. and/or at gas hourly space velocity (GHSV) of ethane between 500-5000 hr$^{-1}$, preferably at GHSV of ethane at 1000 hr$^{-1}$. Additionally, the selective hydrogenating of acetylene to ethylene is performed at temperatures between 20-200° C., preferably between 20-90° C. and/or at GHSV of acetylene between 10-1000 hr$^{-1}$, and a H$_2$/C$_2$H$_2$ ratio between 0.5 to 20, preferably between 2-6.

The benefits of such novel catalysts B and C are discussed further below with respect to the catalytic performance of catalysts A, B, and C in hydrocarbon conversions as illustrated in the selective acetylene hydrogenation reaction, and ethane aromatization reactions, e.g., catalytic hydrogenation of alkynes and alkadienes to olefins and catalytic conversion of ethane to aromatics. Applicant notes that while discussion is made of the catalytic hydrocarbon conversion process to the selective hydrogenating of acetylene to ethylene, such conversion process is not limited to said selective hydrogenating of acetylene to ethylene, but can also include selective hydrogenation of 1,3-butadiene (C$_4$H$_6$) to butene (C$_4$H$_8$). The Pt dispersion in these catalysts were examined by dynamic CO chemisorption measurements. The active phase of these catalysts was studied by CO-DRIFTS, and XANES.

Figure 6:
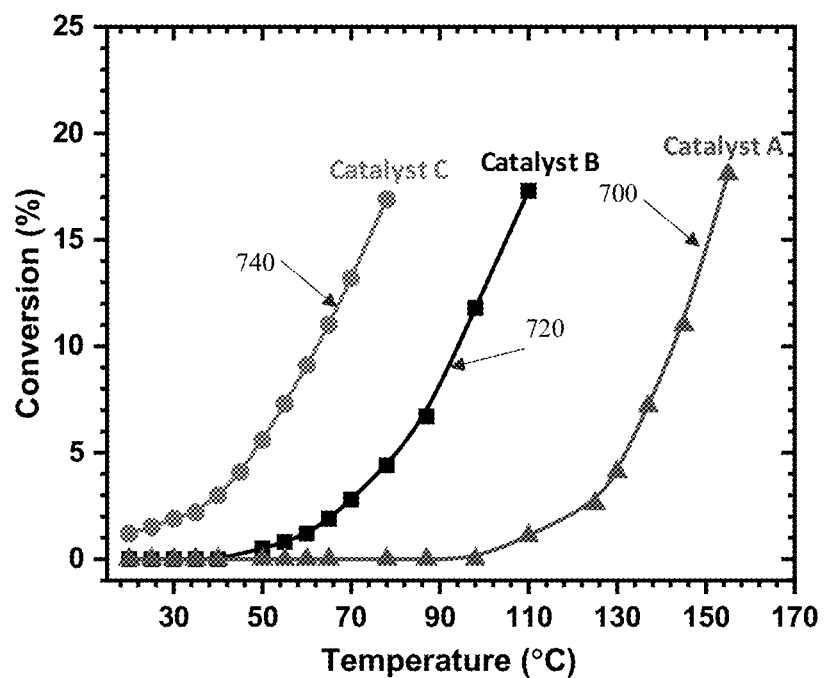
FIG. 6 is a graph illustrating the catalytic performance in terms of acetylene conversion over a prior art catalyst ($Pt/Al_2O_3$ after reduction), of a catalyst embodying the first aspect of the invention (Pt/ZSM-5 after reduction), and a catalyst embodying the second aspect of the invention (Pt/ZSM-5 after ethane activation), in the selective acetylene hydrogenation reaction.

FIG. 6 shows the catalytic performance in terms of acetylene conversion of catalyst A, (Pt/Al$_2$O$_3$ after reduction) (curve 700), catalyst B, (Pt/ZSM-5 after reduction) (curve 720), and catalyst C, (Pt/ZSM-5 after activation) (curve 740), in the selective acetylene hydrogenation reaction. As seen in FIG. 6, catalysts B and C are much more active than catalyst A. For example, at 70° C. with the same platinum loading, the acetylene conversion over catalyst C is 13%, while the conversion over catalyst B is less than 3%. At the same reaction conditions, the acetylene conversion over catalyst A is negligible. On the other hand, the ethylene selectivities of catalysts A, B, and C are similar, at approximately 65%, at the measured temperature range. In these measurements, the same amount of catalyst, 500 mg was used, and the total gas flow was 76 mL/min, with 2 mL/min acetylene, 6 mL/min hydrogen, 2 mL/min nitrogen, and 66 mL/min helium.

Figure 7:
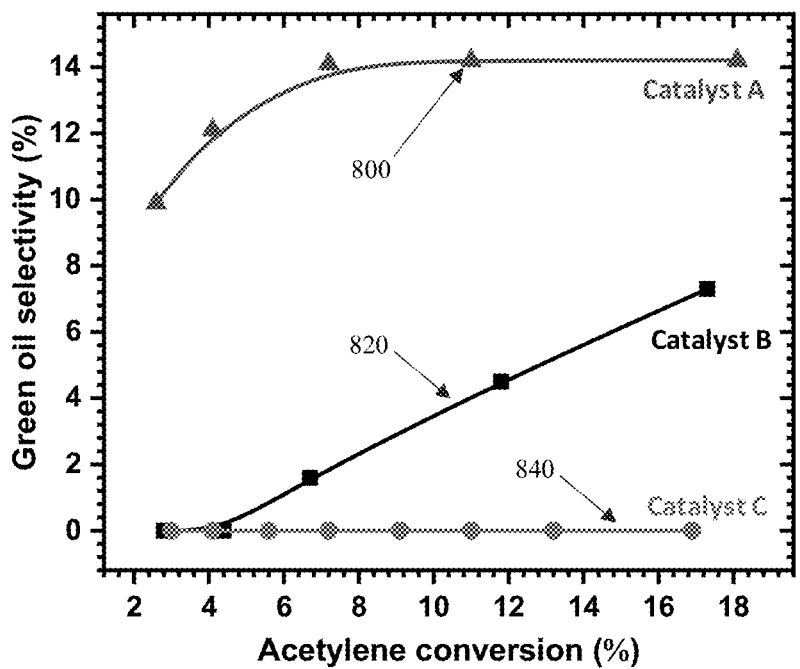
FIG. 7 is a graph showing the green oil selectivity over a prior art catalyst ($Pt/Al_2O_3$ after reduction), a catalyst embodying the first aspect of the invention (Pt/ZSM-5 after reduction), and a catalyst embodying the second aspect of the invention (Pt/ZSM-5 after ethane activation), in the selective acetylene hydrogenation reaction.

FIG. 7 shows the green oil selectivity of catalyst A, (Pt/Al$_2$O$_3$ after reduction) (curve 800), catalyst B, (Pt/ZSM-5 after reduction) (curve 820), and catalyst C, (Pt/ZSM-5 after activation) (curve 840) in the selective acetylene hydrogenation reaction. Clearly, the green oil productivities of catalyst B and catalyst C are much lower than catalyst A. More significantly, the green oil productivity of catalyst C is zero or almost zero. As the presence of green oil products can significantly poison the hydrogenation catalysts, and decrease the lifetime of the catalysts, the reduction of the green oil productivity to a near zero or zero level is a great benefit of catalyst C.

Based on the catalytic results shown in FIG. 6 and FIG. 7, it can be concluded that catalyst B (Pt/ZSM-5 after reduction) is much more active than catalyst A (Pt/Al$_2$O$_3$ after reduction) for the selective hydrogenation of acetylene to ethylene, with similar ethylene selectivity and reduced green oil productivity. However, catalyst C (PtC$_x$/ZSM-5) shows even more improved catalytic activity towards acetylene hydrogenation, with similar ethylene activity and negligible green oil productivity. Overall, catalyst C having the features of this invention exhibits significantly improved catalytic performance in the selective acetylene hydrogenation reaction, in terms of activity and selectivity, compared to catalyst A (standard Pt/Al$_2$O$_3$ catalyst), e.g., the encapsulated platinum carbide nanoclusters are active and selective towards the selective hydrogenation of acetylene to ethylene.

Figure 8:
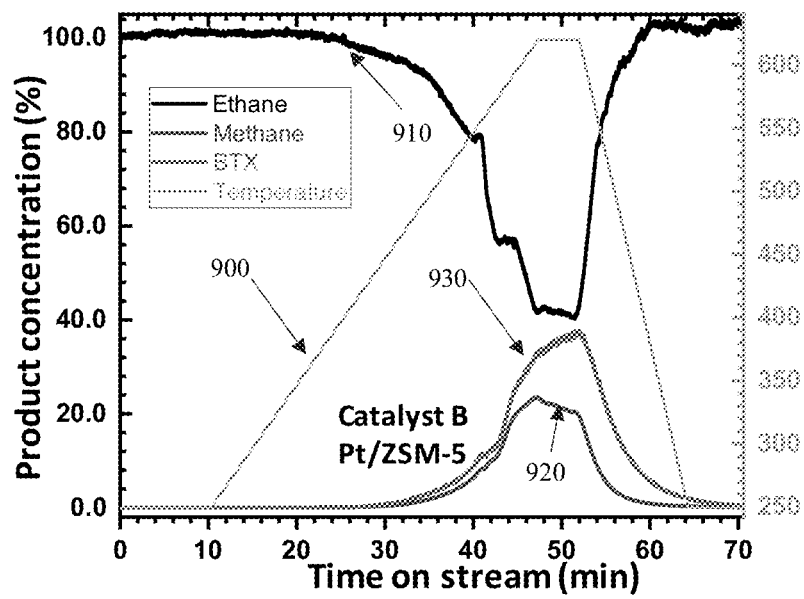
FIG. 8 is a graph showing Temperature-Programmed Surface Reaction data of ethane over a catalyst embodying the first aspect of the invention (Pt/ZSM-5 after reduction), at a temperature range of 250-620° C.

FIG. 8 shows Temperature-Programmed Surface Reaction data of ethane over catalyst B (Pt/ZSM-5 after reduction), at the temperature range of 250-620° C. (curve 900). The product concentrations (based on carbon) of ethane (curve 910), methane (curve 920), and BTX (curve 930) are monitored by a mass spectrometer (MS), and plotted on the Y axis.

Figure 9:
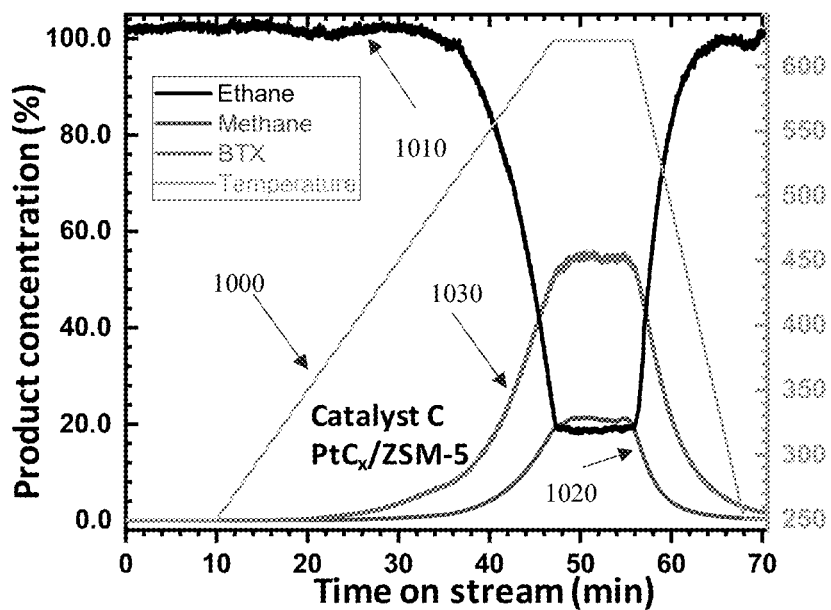
FIG. 9 is a graph showing Temperature-Programmed Surface Reaction data of ethane over a catalyst embodying the second aspect of the invention (Pt/ZSM-5 after ethane activation), at a temperature range of 250-620° C.

FIG. 9 shows Temperature-Programmed Surface Reaction data of ethane over catalyst C (Pt/ZSM-5 after activation), at the temperature range of 250-620° C. (curve 1000). The product concentrations (based on carbon) of ethane (curve 1010), methane (curve 1020), and BTX (curve 1030) are monitored by a mass spectrometer (MS), and plotted on the Y axis.

Figure 10:
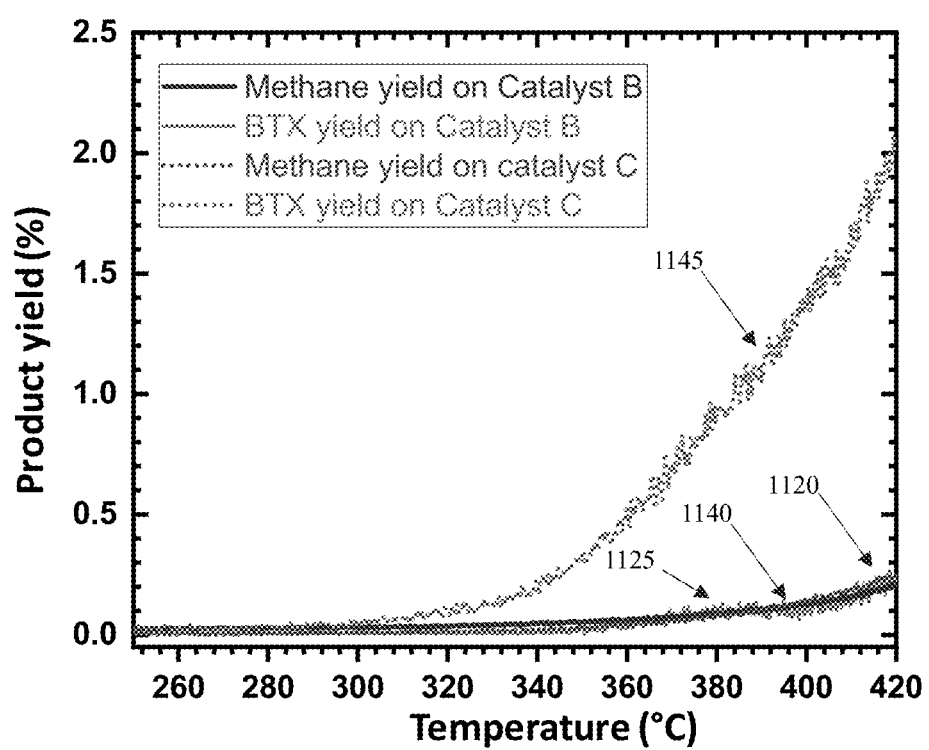
FIG. 10 is a graph displaying the methane and BTX yields as a function of reaction temperatures over a catalyst embodying the first aspect of the invention (Pt/ZSM-5 after reduction), and a catalyst embodying the second aspect of the invention (Pt/ZSM-5 after ethane activation).

FIG. 10 displays the methane and BTX yields as a function of reaction temperatures for catalyst B (curves 1120, 1125, respectively) and the methane and BTX yields as a function of reaction temperatures for catalyst C (curves 1140, 1145, respectively). The figure is plotted based on the data obtained from FIGS. 8 and 9.

FIGS. 8, 9, and 10 show that catalyst C (PtC$_x$/ZSM-5) is highly active for ethane aromatization. For catalyst B (Pt/ZSM-5), the data shows that the light-off temperature is approximately at 400° C., at which Pt carbide species start to form. As the characterization data shows, during ethane aromatization, Pt species are present as Pt carbide nanoclusters, thus an initial introduction period is needed to activate catalyst B. Whereas, for catalyst C, no introduction period is needed. Therefore, for catalyst C, the light-off temperature is approximately at 300° C., which is much lower than catalyst B. In addition, the initial BTX selectivity is much higher for catalyst C than the BTX selectivity for catalyst B. Such observations in combination with characterization data clearly show that in-situ formed confined Pt carbide nanoclusters are the active phase for Pt/ZSM-5 based catalyst in ethane aromatization, e.g., the encapsulated platinum carbide nanoclusters are active and selective towards ethane aromatization.

The measurements also show that mixing the inert binder with Pt/ZSM-5 does not change the catalyst activity and selectivity in the case of catalyst B and catalyst C, for both acetylene hydrogenation and ethane aromatization reactions. Thus, the inert binder does not participate the catalytic reactions of hydrocarbon conversions In conclusion, the data shows that catalyst C (Pt/ZSM-5 after activation) forms novel encapsulated Pt carbide nanoclusters, which has several benefits over the previous hydrogenation catalysts. For example, while not limiting the invention, the benefits include:

1. Metal carbide material can be synthesized at ambient pressure.
2. Metal carbide material can be synthesized at temperatures between 300-650° C.
3. Pt carbide material can be synthesized by using commercially available zeolite supports and Pt precursors, preferably Pt nitrate, without using expensive diamond support and laser heating.
4. Metal carbide can be formed as nanoclusters in the support.

Accordingly, the above embodiments of the invention provided involve at least the following three approaches:
1. Preparation of catalysts with impregnation of zeolite with a metal solution, followed by calcination, reduction, and ethane activation.
2. Illustration of the high catalytic performance of prepared catalysts in catalytic hydrocarbon conversion reactions.
3. Identification of the active phase of the prepared catalysts through various in-situ characterizations.

The above description is merely the various embodiments of the present invention, where the scope of the invention is not limited thereto, and changes or substitutions within the technical scope of the invention can be easily made by those persons skilled in the art and should be considered to be within scope of the present invention. Therefore, the scope of protection of the present invention is only subject to the scope of protection of the appended claims.

The invention claimed is:

1. A catalytic process using a metal carbide nanomaterial comprising steps of:
    preparing the metal carbide nanomaterial comprising a support and a plurality of metal carbide nanoclusters encapsulated in a plurality of micropores of the support; and
    performing a catalytic hydrocarbon conversion process using the metal carbide nanomaterial,
    wherein the catalytic hydrocarbon conversion process is catalytic hydrogenation of acetylene to ethylene, and the metal carbide nanomaterial contains 500 ppm of platinum,
    wherein the catalytic hydrogenation of acetylene to ethylene is performed at a temperature between 20 to 200° C., a gas hourly space velocity (GHSV) of acetylene between 10 to 1000 hr$^{-1}$, and a H$_2$/C$_2$H$_2$ volume ratio between 0.5 to 20,
    wherein the metal carbide nanomaterial is prepared by a method comprising the following steps:
    Step 1: mixing ZSM-5 powder having a silica to alumina molar ratio of 30 in a solution of Pt(NO$_3$)$_2$ to form a mixture;
    Step 2: drying the mixture to form a dry product;
    Step 3: calcinating the dry product at 550° C. for 4 hours;
    Step 4: reducing the dry product in hydrogen at 630° C. for 1 hour;
    Step 5: forming a catalyst comprising encapsulated metal nanoclusters within the support; and
    Step 6: activating the catalyst at 300~500° C. in an ethane atmosphere balanced with 50% by volume of nitrogen.

2. The catalytic process according to claim 1, wherein the encapsulated metal carbide nanoclusters have a size close to 1 nm.

3. The catalytic process according to claim 1, wherein the metal carbide nanomaterial has a platinum dispersion greater than 90%.

4. The catalytic process according to claim 1, wherein the catalytic hydrogenation of acetylene to ethylene is performed at a temperature between 20 to 90° C.

* * * * *